United States Patent
Yang et al.

(10) Patent No.: US 11,666,370 B2
(45) Date of Patent: Jun. 6, 2023

(54) APPARATUS AND METHOD FOR TARGETED TEMPORARY BRONCHIAL NERVE MODULATION BY CRYO-ABLATION FOR PREVENTION AND TREATMENT OF ACUTE RESPIRATORY DISTRESS SYNDROMES

(71) Applicant: Medtronic, Inc., Minneapolis, MN (US)

(72) Inventors: Zhongping Yang, Woodbury, MN (US); Randal C. Schulhauser, Phoenix, AZ (US); Nicolas Coulombe, Anjou (CA); Jean-Pierre Lalonde, Candiac (CA); Anthony Rorvick, Champlin, MN (US)

(73) Assignee: Medtronic, Inc., Minneapolis, MN (US)

( * ) Notice: Subject to any disclaimer, the term of this patent is extended or adjusted under 35 U.S.C. 154(b) by 350 days.

(21) Appl. No.: 16/939,162

(22) Filed: Jul. 27, 2020

(65) Prior Publication Data
US 2022/0022931 A1   Jan. 27, 2022

(51) Int. Cl.
*A61B 18/02* (2006.01)
*A61B 18/00* (2006.01)

(52) U.S. Cl.
CPC .... *A61B 18/02* (2013.01); *A61B 2018/00255* (2013.01); *A61B 2018/00541* (2013.01);
(Continued)

(58) Field of Classification Search
CPC .......... A61B 18/02; A61B 2018/00255; A61B 2018/0054; A61B 2018/0212; A61B 2018/0022
See application file for complete search history.

(56) References Cited

U.S. PATENT DOCUMENTS

| 7,412,977 B2 | 8/2008 | Fields et al. |
| 7,938,123 B2 | 5/2011 | Danek et al. |

(Continued)

FOREIGN PATENT DOCUMENTS

| EP | 3120792 A1 | 1/2017 |
| EP | 3244820 B1 | 6/2020 |

(Continued)

OTHER PUBLICATIONS

Keningsberg, Quantification of the cryoablation zone demarcated by pre- and postprocedural electroanatomic mapping in patients with atrial fibrillation using the 28-mm second-generation cryoballoon, Feb. 2015, Heart Rhythm, vol. 12 Issue 2, pp. 283-290 (Year: 2015).*

(Continued)

*Primary Examiner* — Linda C Dvorak
*Assistant Examiner* — Abigail Bock
(74) *Attorney, Agent, or Firm* — Michael Best & Friedrich, LLP

(57) ABSTRACT

A method of treating or preventing acute respiratory distress syndromes (ARDS) includes advancing a cryogenic treatment element into a target bronchus of a mammal and exchanging cryogenic energy between the target bronchus and the cryogenic treatment element for a predetermined period of time until a target temperature of the target bronchus is reached to cause neuropraxia of nerves within the target bronchus.

14 Claims, 5 Drawing Sheets

(52) U.S. Cl.
CPC ............... *A61B 2018/00577* (2013.01); *A61B 2018/00994* (2013.01); *A61B 2018/0212* (2013.01)

(56) References Cited

U.S. PATENT DOCUMENTS

| | | | |
|---|---|---|---|
| 8,088,127 B2 | 1/2012 | Mayse et al. | |
| 9,095,321 B2 | 8/2015 | Phelan et al. | |
| 9,144,449 B2 | 9/2015 | Burr et al. | |
| 10,328,281 B2 | 6/2019 | Stopek | |
| 2007/0255162 A1 | 11/2007 | Abboud et al. | |
| 2008/0312644 A1 | 12/2008 | Fourkas et al. | |
| 2009/0076439 A1* | 3/2009 | Dollar | A61M 25/1018 604/97.03 |
| 2009/0192505 A1 | 7/2009 | Askew et al. | |
| 2009/0205665 A1 | 8/2009 | Tanaka et al. | |
| 2009/0299355 A1 | 12/2009 | Bencini et al. | |
| 2010/0249765 A1 | 9/2010 | Johnston | |
| 2012/0136418 A1* | 5/2012 | Buckley | A61B 18/02 607/105 |
| 2012/0310226 A1 | 12/2012 | Fourkas et al. | |
| 2013/0345688 A1* | 12/2013 | Babkin | A61B 18/02 606/20 |
| 2014/0276781 A1* | 9/2014 | Beani | A61B 17/42 606/41 |
| 2015/0141813 A1 | 5/2015 | Weadock | |
| 2015/0173673 A1 | 6/2015 | Toth et al. | |
| 2015/0265334 A1 | 9/2015 | Franke et al. | |
| 2015/0272666 A1 | 10/2015 | Wang | |
| 2017/0319853 A1 | 11/2017 | Yamasaki et al. | |
| 2019/0026056 A1 | 1/2019 | Wang et al. | |
| 2019/0262056 A1 | 8/2019 | Yang et al. | |
| 2019/0365452 A1 | 12/2019 | Avitall et al. | |
| 2020/0000514 A1 | 1/2020 | Weadock | |
| 2020/0060758 A1* | 2/2020 | Rajagopalan | A61B 18/1492 |
| 2020/0129220 A1 | 4/2020 | Jung | |

FOREIGN PATENT DOCUMENTS

| | | |
|---|---|---|
| WO | 2012019156 A1 | 2/2012 |
| WO | 2012027641 A2 | 3/2012 |
| WO | 2015120325 A1 | 8/2015 |
| WO | 2016033017 A1 | 3/2016 |
| WO | 2016109437 A1 | 7/2016 |
| WO | 2017214183 A1 | 12/2017 |

OTHER PUBLICATIONS

International Search Report dated May 16, 2019, for International Application No. PCT/CA2019/050226 filed on Feb. 26, 2019; Consisting of 8 pages.

European Patent Office, Supplementary European Search Report, dated Nov. 2, 2021, for corresponding European Application No. EP 19761431; consisting of 7 pages.

Yan-Lin Yang, et al., Optimal Esophageal Balloon Volume for Accurate Estimation of Pleural Pressure at End-Expiration and End-Inspiration: an in Vitro Bench Experiment, Intensive Care Medicine Experimental, Aug. 2, 2017 (Aug. 2, 2017), DOI: 10.1186/s40635-017-0148-z, 12 pages.

International Search Report and Written Opinion dated Nov. 4, 2021, for corresponding International Application No. PCT/US2021/043178; International Filing Date: Jul. 26, 2021, consisting of 181-pages.

* cited by examiner

APPARATUS AND METHOD FOR TARGETED TEMPORARY BRONCHIAL NERVE MODULATION BY CRYO-ABLATION FOR PREVENTION AND TREATMENT OF ACUTE RESPIRATORY DISTRESS SYNDROMES

CROSS-REFERENCE TO RELATED APPLICATION n/a.

FIELD

The present technology is generally related to methods for causing neuropraxia in nerves in a bronchus for treatment of acute respiratory distress syndrome (ARDS).

BACKGROUND

ARDS is a form of severe hypoxemic respiratory failure characterized by excessive pro-inflammatory lung injury to the alveolar capillary barrier with extravasation of protein-rich edema fluid into the airspace owing to a viral infection, such as COVID-19, or a bacterial infection. However, systemic host immune/inflammatory response in respiratory infections is critical to cure the body of the viral or bacterial infection.

SUMMARY

The techniques of this disclosure generally relate to methods for causing neuropraxia in nerve in a bronchus for treatment or prevention of ARDS.

In one aspect, a method of treating or preventing ARDS includes advancing a cryogenic treatment element into a target bronchus of a mammal and exchanging cryogenic energy between the target bronchus and the cryogenic treatment element for a predetermined period of time until a target temperature of the target bronchus is reached to cause neuropraxia of nerves within the target bronchus.

In one aspect of this embodiment, the cryogenic treatment element includes a balloon, and wherein a diameter and length of the balloon is adjustable.

In one aspect of this embodiment, the balloon is one from the group consisting of fixed in diameter and length and adjustable in diameter and length between 5 mm and 40 mm.

In one aspect of this embodiment, the method further includes inflating the balloon with at least one from the group consisting of liquid nitrogen, argon nitrogen dioxide, and supercritical fluid, and calculating a diameter of the target bronchus based on a measured internal pressure within the balloon.

In one aspect of this embodiment, calculating the diameter of the target bronchus further includes calculating an inflection point between the measured internal pressure within the balloon and a volume of fluid within the balloon.

In one aspect of this embodiment, the method further includes inflating the balloon to a target inflation diameter based on the calculated diameter of the target bronchus.

In one aspect of this embodiment, inflating the balloon to a target inflation diameter includes adjusting a coolant flow rate into the balloon based on the target inflation diameter.

In one aspect of this embodiment, the target temperature of the bronchus is between 10 degrees Celsius and −120 degrees Celsius.

In one aspect of this embodiment, the predetermined period of time is between 1 and 300 seconds.

In one aspect of this embodiment, the method further includes exchanging cryogenic energy with the target bronchus until a lesion depth of at least 3 mm is achieved.

In one aspect, a method of treating or preventing acute respiratory distress syndrome includes advancing a catheter having a proximal end and a distal end, the distal end having a balloon, into a target bronchus of a mammal and exchanging cryogenic energy between the balloon and the target bronchus for a predetermined period of time until a target temperature of the target bronchus is reached to cause neuropraxia of nerves within the bronchus.

In one aspect of this embodiment, a diameter and length of the balloon is adjustable.

In one aspect of this embodiment, the balloon is adjustable in diameter and length between 5 mm and 40 mm.

In one aspect of this embodiment, the method further includes inflating the balloon with at least one coolant from the group consisting of liquid nitrogen, argon nitrogen dioxide, and supercritical fluid and calculating a diameter of the target bronchus based on a measured internal pressure within the balloon.

In one aspect of this embodiment, calculating the diameter of the target bronchus further includes calculating an inflection point between the measured internal pressure within the balloon and a volume of fluid within the balloon.

In one aspect of this embodiment, the method further includes inflating the balloon to a target inflation diameter based on the calculated diameter of the target bronchus.

In one aspect of this embodiment, inflating the balloon to a target inflation diameter includes adjusting a coolant flow rate into the balloon based on the target inflation diameter.

In one aspect of this embodiment, the target temperature of the target bronchus is between 10 degrees Celsius and −120 degrees Celsius.

In one aspect of this embodiment, the predetermined period of time is between 1 and 300 seconds.

In one aspect, a method of treating or preventing acute respiratory distress syndrome, includes advancing a catheter having a proximal end and a distal end, the distal end having a balloon, into a target bronchus of a mammal. The balloon is inflated with at least one coolant from the group consisting of liquid nitrogen, argon, supercritical fluid, and nitrogen dioxide. A diameter of the target bronchus is calculated based on a measured internal pressure within the balloon including calculating an inflection point between the measured internal pressure within the balloon and a volume of fluid within the balloon. The balloon is inflated to a target inflation diameter based on the calculated diameter of the target bronchus. Cryogenic energy is exchanged between the balloon and the target bronchus for a range of 1-300 seconds until a temperature range of 10 degrees Celsius to −120 degrees Celsius of the bronchus is reached to cause neuropraxia of nerves within the bronchus.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
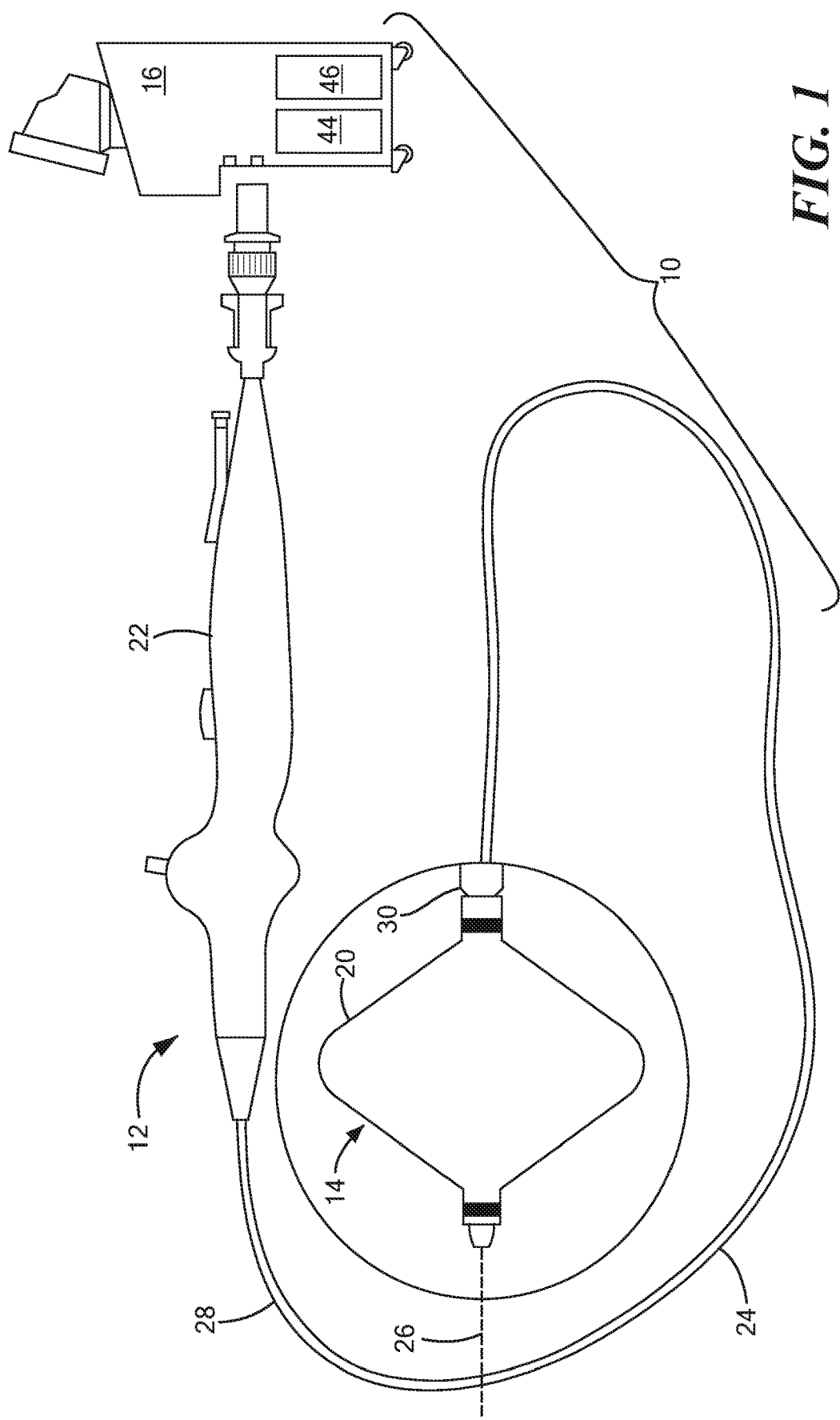
FIG. 1 shows an exemplary system for bronchial denervation; the system including a cryoablation device.

Referring now to FIG. 1, an exemplary medical system 10 for bronchial modulation is shown. As used herein, modulation refers to ablation to cause a temporary conduction block in one or more nerves that recovers over time. In one embodiment, the medical system 10 generally includes a treatment device, such as a cryoablation device 12, having one or more treatment elements 14, and a control unit 16 in communication with the cryoablation device 12. Although the cryoablation device 12 is described herein as operating to reduce the temperature of target tissue in order to modulate nerves within the lungs, it will be understood that the cryoablation device 12 also may be used with one or more additional modalities, such as radiofrequency (RF) ablation, pulsed field ablation, ultrasound ablation, microwave ablation, or the like. Additionally, the cryoablation device 12 may be used for nerve modulation of other locations within the patient's body, such as the heart.

The one or more treatment elements 14 are configured to deliver cryogenic therapy, and may further be configured to deliver radiofrequency energy, pulsed field ablation energy, or the like for energetic transfer with the area of targeted tissue, such as pulmonary tissue. In particular, the treatment element(s) 14 are configured to reduce the temperature of adjacent tissue in order to perform cryogenic treatment and consequently, nerve modulation. For example, the treatment elements(s) 14 may include one or more balloons 20 (as shown in FIG. 1), which may be compliant or non-compliant, within which a coolant, such as liquid nitrogen, argon, supercritical fluid, or nitrogen dioxide may be circulated in order to reduce the temperature of the balloon 20. Additionally, the treatment element(s) 14 may include other thermally and/or electrically-conductive components, such as one or more electrodes in communication with the control unit 16 (not shown).

Figure 2:
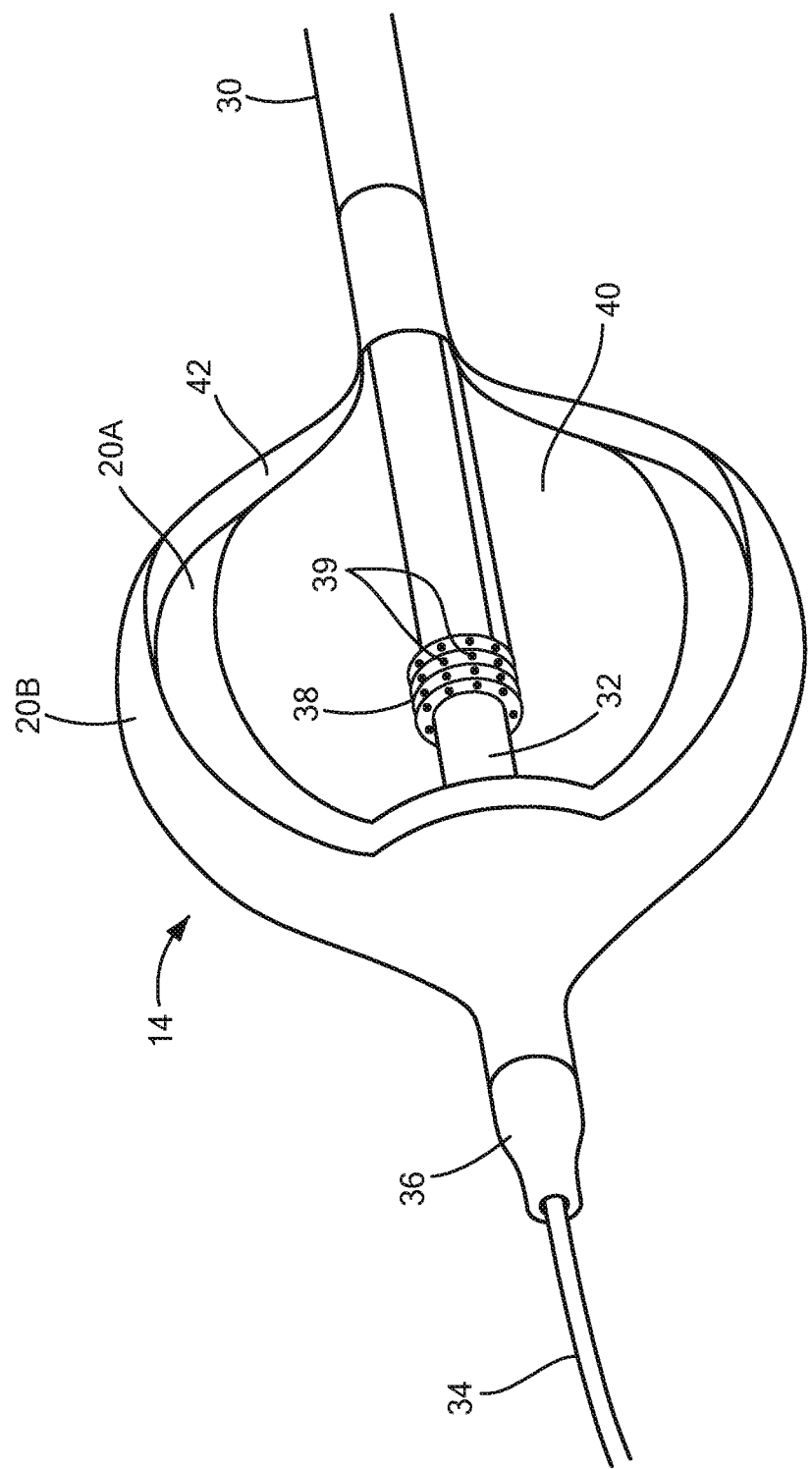
FIG. 2 shows a partial cross-sectional view of an exemplary cryoablation device in accordance with the present disclosure.

In the embodiment shown in FIGS. 1 and 2, the cryoablation device 12 includes a handle 22 and an elongate body 24 coupled to the handle 22. The elongate body 24 is sized and configured to be passable through a patient's bronchus and/or positionable proximate to a tissue region for diagnosis or treatment, such as a catheter, sheath, or intravascular introducer. The elongate body 24 defines a longitudinal axis 26, a proximal portion 28, and a distal portion 30, and may further include one or more lumens disposed within the elongate body 24 that provide mechanical, electrical, and/or fluid communication between the proximal portion 28 of the elongate body 24 and the distal portion 30 of the elongate body 24. Further, the treatment element(s) 14 (such as the balloon(s) 20 shown in FIGS. 1 and 2) are coupled to the elongate body distal portion 30. In one embodiment, the cryoablation device 12 further includes a shaft 32 longitudinally movable within a lumen of the elongate body 24, such that the shaft 32 may be advanced or retracted within the elongate body 24, and this movement of the shaft 32 may affect the shape and configuration of the treatment element(s) 14. That is the length and diameter of the of balloon 20 may be adjustable or fixed. For example, the cryoablation device 12 may include one treatment element 14, and the shaft 32 may be fully advanced when the treatment element 14 is deflated and in a delivery (or first) configuration wherein the treatment element 14 has a minimum diameter suitable, for example, for retraction of the cryoablation device 12 within a sheath for delivery to and removal from the targeted tissue site. Conversely, when the treatment element 14 is inflated or expanded and in a treatment (or second) configuration, the shaft 32 may be advanced or retracted over a distance that affects the size and configuration of the inflated or expanded treatment element 14. Further, the shaft 32 may include a guidewire lumen through which a sensing device, mapping device, guidewire 34, or other system component may be located and extended from the distal end of the cryoablation device 12 (for example, from the distal portion 36 of the shaft 32). When expanded, the treatment element(s) 14 are sized and configured to fit within a targeted bronchus. For example, the expanded treatment element(s) 14 may have a maximum outer diameter and length of between approximately 5 mm and approximately 40 mm (±2 mm).

In one embodiment, the treatment element 14 includes two balloons: an inner (or first) balloon 20A and an outer (or second) balloon 20B. However, it will be understood that the treatment element 14 may include any number of balloons. In the embodiment shown in FIG. 2, a proximal portion of the treatment element 14 is coupled to the distal portion 30 of the elongate body 24 and a distal portion of the treatment element 14 is coupled to a distal portion 36 of the shaft 32. The cryoablation device 12 also includes one or more nozzles, orifices, or other fluid delivery elements 38 for delivering fluid (for example, coolant) to an interior chamber 40 of the treatment element 14 for equatorial distribution. Equatorial distribution refers to coolant being delivered at the largest diameter around an imaginary circle within the treatment element 14. For example, fluid may be delivered to the interior chamber 40 of the inner balloon 20A and/or to the interior chamber of the outer cryoballoon 20B (that is, to the interstitial space 42 between the inner 20A and outer 20B balloons). For simplicity, coolant will be referred to herein as being delivered to the interior chamber 40 of the treatment element 14. During operation, coolant may flow from a coolant supply reservoir 44 through a coolant delivery conduit within the elongate body 24 of the cryoablation device 12 to the distal portion 30, where the coolant may then enter the interior chamber 40 of the treatment element 14, such as through the one or more fluid delivery elements 38, where the coolant expands as it absorbs heat. Expanded coolant may then pass from the interior chamber 40 of the treatment element 14 to a coolant recovery reservoir 46 and/or scavenging system through a coolant recovery conduit. Further details about the cryoablation device 12 may be found in U.S. Patent Publication No. US2019/026056, the entirety of which is expressly incorporated by reference herein.

Figure 3:
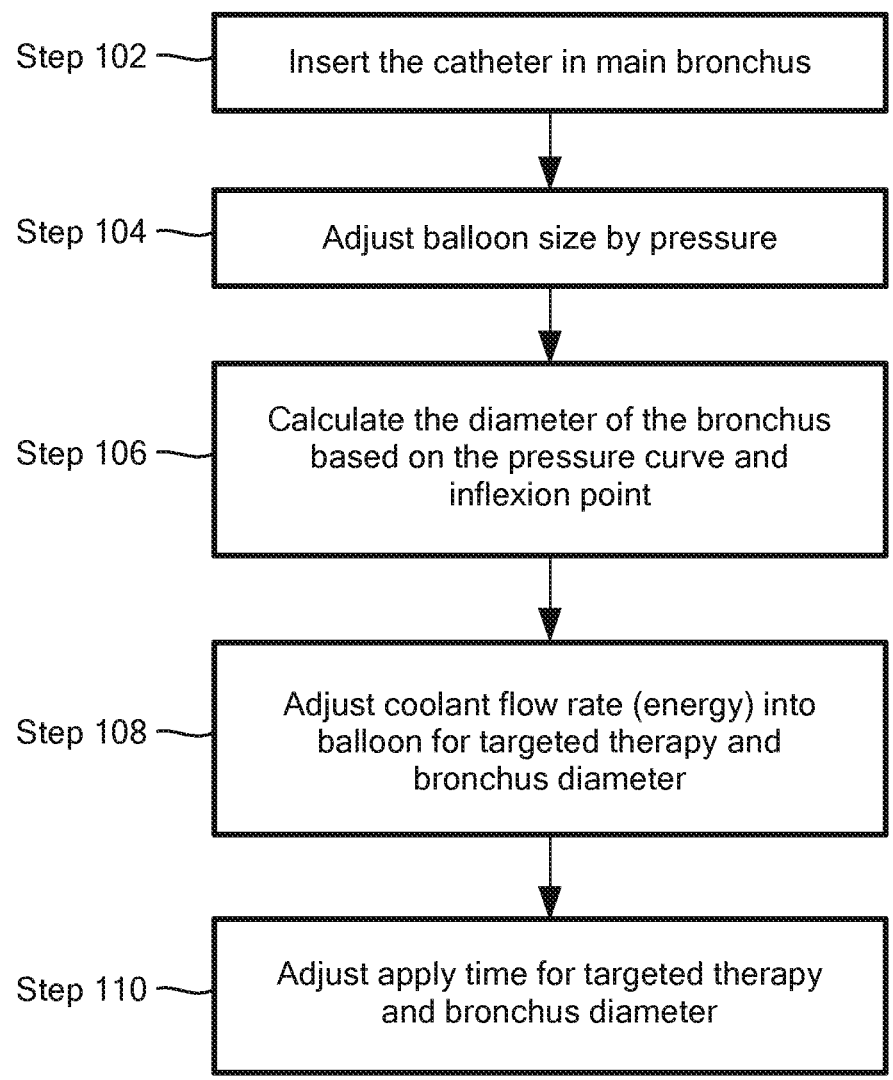
FIG. 3 shows a flow chart of the steps for causing neuropraxia within a bronchus.
Figure 4B:
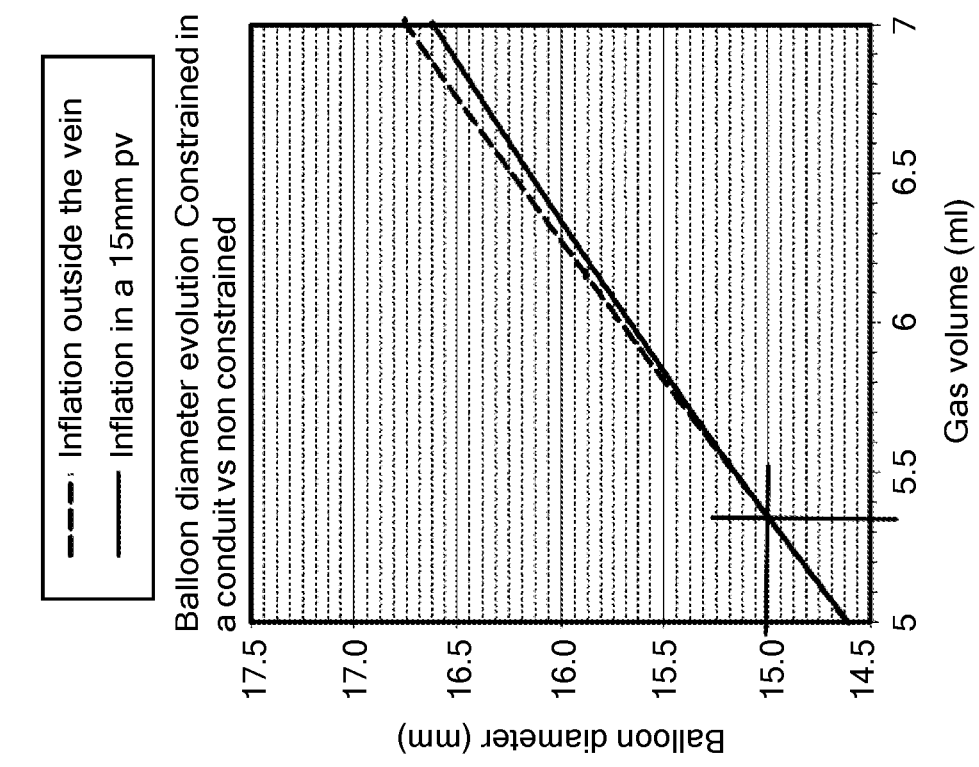
FIG. 4B is a graph of balloon diameter versus gas volume within a constrained space and outside of a constrained space.
Figure 4A:
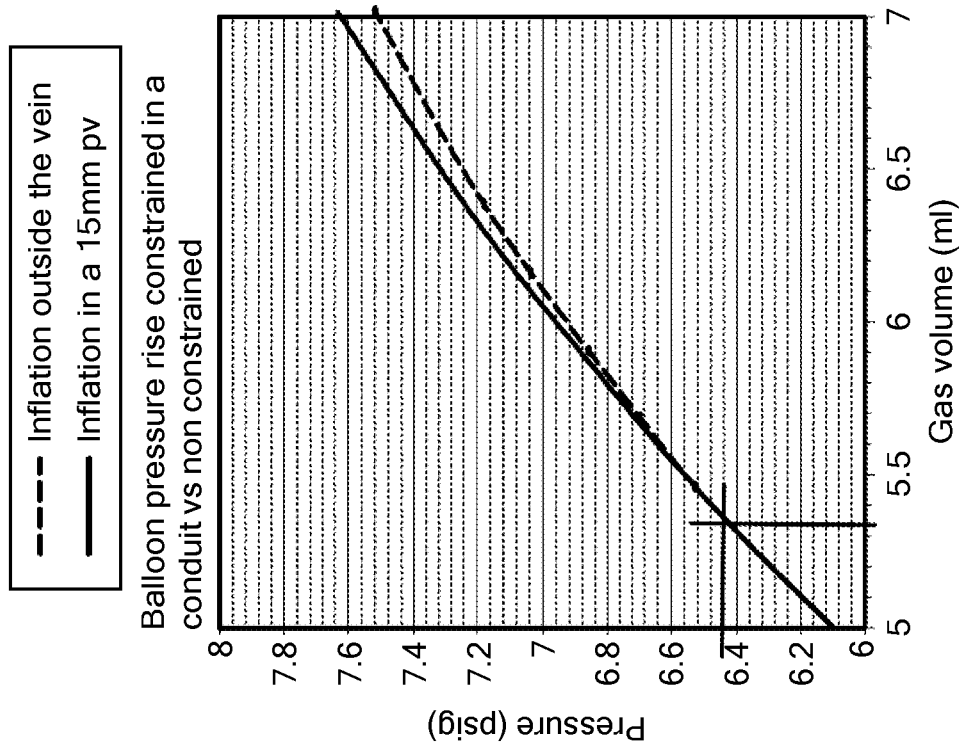
FIG. 4A is a graph of a pressure versus gas volume within a constrained space and outside of a constrained space.
Figure 5:
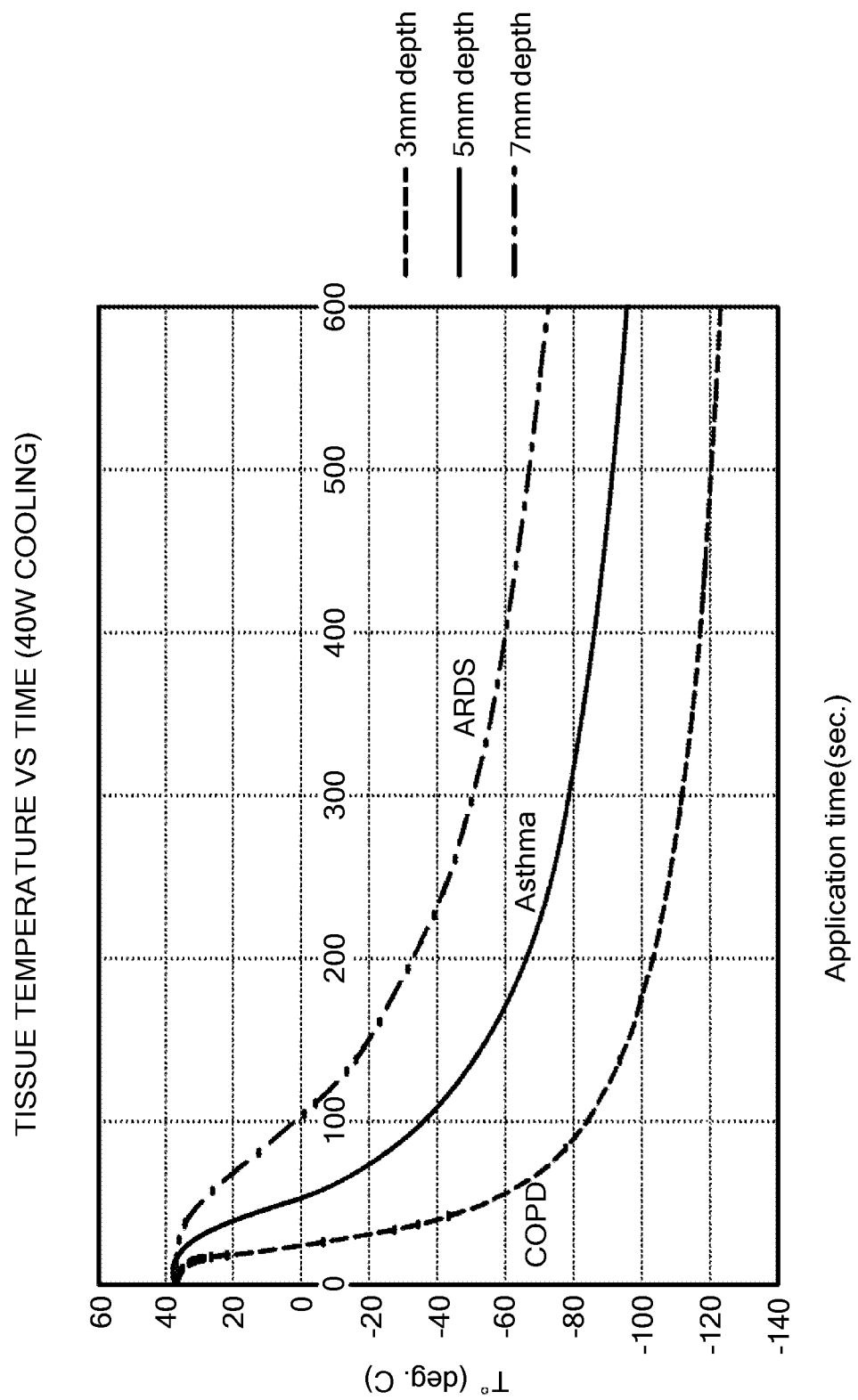
FIG. 5 is a graph showing temperature versus application time for various respiratory conditions and for achieving a certain lesion depth.

Referring now to FIG. 3 in which an exemplary method of modulating bronchus nerves is shown. The treatment element 14, which may include one or more balloons 20, is advanced into a target bronchus (Step 102). In an exemplary configuration, the cryoablation device shown in FIGS. 1 and 2 is advanced, for example, through the mouth of the mammal and into a target bronchus. The balloon 20 may be inflated with either liquid nitrogen, nitrogen dioxide, supercritical fluid, such as argon, or similar coolants, and a diameter of the target bronchus is calculated based on a measured internal pressure within the balloon 20 (Step 104). In particular, as shown in FIGS. 4A-4B the volume of inflation fluid within the balloon generally increases linearly with the internal pressure within the balloon. However, when the balloon 20 is placed within a constrained spaced, such as a vein or the bronchus, compared to an unconstrained space, the pressure curve and volume of inflation fluid curve begin to diverge and a particular point identified as an inflection point. The internal pressure at this inflection point is measured and correlated into a measure of balloon 20 diameter. Knowing the diameter of the bronchus, or any particular conduit, allows for delivery of the proper dose of coolant to treat. In particular, for a given tissue thickness, a larger conduit requires less time to cool, but requires a higher coolant flow. Moreover, arterial damage may be prevented by operating at the minimum required pressure to achieve apposition. The balloon 20 is then inflated to a target inflation diameter based on the calculated diameter of the target bronchus (Step 106). This can be achieved by adjusting the coolant flow rate and/or the injection pressure and return flow into and out of the balloon 20. Cryogenic energy is exchanged with the target bronchus for a predetermined period of time until a target temperature within the target bronchus is reached to cause neuropraxia of nerves within the bronchus (Step 108). In an exemplary configuration, as shown in FIG. 5, cryogenic energy is applied from 1 to 300 seconds until a temperature of 10 degrees Celsius to −120 degrees Celsius is reached in the bronchus to cause neuropraxia (Step 110). In some configurations, cryogenic energy is further applied until a lesion of between 3 mm and 7 mm is achieved. Neurapraxia of bronchial nerves may result in anti-inflammatory and anticholinergic effects within the lungs.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of treating or preventing acute respiratory distress syndrome, comprising:
   advancing a cryogenic treatment element including a balloon into a target bronchus of a mammal;
   calculating a diameter of the target bronchus based on a measured internal pressure within the balloon by calculating an inflection point between the measured internal pressure within the balloon and a volume of coolant fluid within the balloon;
   inflating the balloon with coolant fluid to a target inflation diameter based on the calculated diameter of the target bronchus; and
   exchanging cryogenic energy between the target bronchus and the cryogenic treatment element for a predetermined period of time until a target temperature of the target bronchus is reached to cause neuropraxia of nerves within the target bronchus,
   wherein inflating the balloon to the target inflation diameter includes adjusting a flow rate of the coolant fluid flowing into the balloon based on the target inflation diameter to reach a minimum required injection pressure to achieve apposition of the target bronchus.

2. The method of claim 1, wherein a diameter and length of the balloon is adjustable.

3. The method of claim 2, further including inflating the balloon with at least one from the group consisting of liquid nitrogen, argon, nitrogen dioxide, and supercritical fluid.

4. The method of claim 1, wherein the balloon is one from the group consisting of fixed in diameter and length and adjustable in diameter and length between 5 mm and 40 mm.

5. The method of claim 1, wherein the target temperature of the bronchus is between 10 degrees Celsius and −120 degrees Celsius.

6. The method of claim 1, wherein the predetermined period of time is between 1 and 300 seconds.

7. The method of claim 1, further including exchanging cryogenic energy with the target bronchus until a lesion depth of at least 3 mm is achieved.

8. A method of treating or preventing acute respiratory distress syndrome, comprising:
   advancing a catheter having a proximal end and a distal end, the distal end having a balloon, into a target bronchus of a mammal;
   calculating a diameter of the target bronchus based on a measured internal pressure within the balloon by calculating an inflection point between the measured internal pressure within the balloon and a volume of fluid within the balloon;
   inflating the balloon with fluid to a target inflation diameter based on the calculated diameter of the target bronchus; and exchanging cryogenic energy between the balloon and the target bronchus for a predetermined period of time until a target temperature of the target bronchus is reached to cause neuropraxia of nerves within the bronchus wherein inflating the balloon to the target inflation diameter includes adjusting a flow rate of the coolant fluid flowing into the balloon based on the target inflation diameter to reach a minimum required injection pressure to achieve apposition of the target bronchus.

9. The method of claim 8, wherein a diameter and length of the balloon is adjustable.

10. The method of claim 9, further including inflating the balloon with at least one coolant from the group consisting of liquid nitrogen, argon, nitrogen dioxide, and supercritical fluid.

11. The method of claim 8, wherein the balloon is adjustable in diameter and length between 5 mm and 40 mm.

12. The method of claim 8, wherein the target temperature of the target bronchus is between 10 degrees Celsius and −20 degrees Celsius.

13. The method of claim 8, wherein the predetermined period of time is between 1 and 300 seconds.

14. A method of treating or preventing acute respiratory distress syndrome, comprising:

advancing a catheter having a proximal end and a distal end, the distal end having a balloon, into a target bronchus of a mammal;

inflating the balloon with at least one coolant from the group consisting of liquid nitrogen, supercritical fluid, argon, and nitrogen dioxide;

calculating a diameter of the target bronchus based on a measured internal pressure within the balloon including calculating an inflection point between the measured internal pressure within the balloon and a volume of fluid within the balloon;

inflating the balloon to a target inflation diameter based on the calculated diameter of the target bronchus; and exchanging cryogenic energy between the balloon and the target bronchus for a range of 1-300 seconds until a temperature range of 10 degrees Celsius to −120 degrees Celsius of the bronchus is reached to cause neuropraxia of nerves within the bronchus wherein inflating the balloon to the target inflation diameter includes adjusting a flow rate of the coolant fluid flowing into the balloon based on the target inflation diameter to reach a minimum required injection pressure to achieve apposition of the target bronchus.

* * * * *